United States Patent
Pena et al.

(10) Patent No.: US 8,400,171 B2
(45) Date of Patent: Mar. 19, 2013

(54) TRANSMISSION LINE MOISTURE SENSOR

(75) Inventors: Gerardo Pena, Seattle, WA (US); Justin D. Kearns, Seattle, WA (US); Jason P. Bommer, Tacoma, WA (US); Matthew K. Fay, Wentzville, MO (US)

(73) Assignee: The Boeing Company, Chicago, IL (US)

( * ) Notice: Subject to any disclaimer, the term of this patent is extended or adjusted under 35 U.S.C. 154(b) by 355 days.

(21) Appl. No.: 12/750,496

(22) Filed: Mar. 30, 2010

(65) Prior Publication Data
US 2010/0182023 A1 Jul. 22, 2010

Related U.S. Application Data

(63) Continuation-in-part of application No. 11/941,367, filed on Nov. 16, 2007, now Pat. No. 8,054,092, and a continuation-in-part of application No. 12/273,014, filed on Nov. 18, 2008, now Pat. No. 8,040,243.

(51) Int. Cl.
G01R 27/08 (2006.01)
(52) U.S. Cl. ..................................... 324/694
(58) Field of Classification Search ............ 324/694
See application file for complete search history.

(56) References Cited

U.S. PATENT DOCUMENTS

| | | | |
|---|---|---|---|
| 4,087,800 A | 5/1978 | Lee | |
| 4,587,517 A | 5/1986 | Engstrom et al. | |
| 5,936,525 A | 8/1999 | Leyden et al. | |
| 6,961,529 B2 * | 11/2005 | Kosuge | 399/176 |
| 7,025,817 B2 * | 4/2006 | Kanke et al. | 106/31.51 |
| 7,132,943 B2 | 11/2006 | Nelson | |
| 7,231,826 B2 | 6/2007 | Bossi et al. | |
| 7,333,898 B2 | 2/2008 | Griess et al. | |
| 7,388,166 B2 | 6/2008 | Marmaropoulos et al. | |
| 7,434,480 B2 | 10/2008 | Georgeson et al. | |
| 7,791,489 B2 * | 9/2010 | Gelbman et al. | 340/572.8 |
| 2002/0145529 A1 | 10/2002 | Kuzik et al. | |
| 2006/0144997 A1 | 7/2006 | Schmidt et al. | |
| 2007/0125189 A1 | 6/2007 | Bossi et al. | |
| 2007/0144272 A1 | 6/2007 | Yu et al. | |

(Continued)

FOREIGN PATENT DOCUMENTS

| | | |
|---|---|---|
| JP | 1054244 | 8/1987 |
| JP | 2005055331 | 8/2003 |

(Continued)

OTHER PUBLICATIONS

Greene, "Sensors Without Batteries," http://www.technologyreview.com/read_article.aspx?id=16864&ch=infotech&a=f, Technology Review Published by MIT, May 15, 2006.

(Continued)

*Primary Examiner* — Jeff Natalini
(74) *Attorney, Agent, or Firm* — Canady & Lortz LLP; Bradley K. Lortz

(57) ABSTRACT

A sensor device for monitoring and testing for potential corrosion of structural elements is disclosed comprising a soluble material disposed adjacent to at least one conductor in a transmission line that reacts to the presence of moisture causing a detectable change in an electrical property of the conductor. The conductor may comprise a conductive ink that is disrupted when the soluble material dissolves beneath it. Alternately, the nonconductive soluble membrane may separate two conductors and moisture causes a disruption in the soluble membrane allowing the two conductors to short. Detected changes in the electrical properties of the one or more conductors can be used to indicate potential corrosion or structural imparement in the structural element. Connection to the sensor device may be through a connector or using a wireless reader which remotely energizes the sensor device comprising one or more RFID chips.

16 Claims, 12 Drawing Sheets

U.S. PATENT DOCUMENTS

| | | |
|---|---|---|
| 2007/0252718 A1 | 11/2007 | Ray |
| 2008/0109187 A1 | 5/2008 | Kollgaard et al. |
| 2008/0163670 A1 | 7/2008 | Georgeson |
| 2008/0167833 A1 | 7/2008 | Matsen et al. |
| 2008/0223152 A1 | 9/2008 | Georgeson et al. |
| 2008/0300559 A1* | 12/2008 | Gustafson et al. ............ 604/361 |
| 2009/0206853 A1* | 8/2009 | Hawkins ....................... 324/696 |

FOREIGN PATENT DOCUMENTS

| | | | |
|---|---|---|---|
| JP | 2007292747 | | 3/2006 |
| WO | WO94/09354 | | 4/1994 |
| WO | WO 2007/069945 | * | 6/2007 |

OTHER PUBLICATIONS

Eckfeldt, "What Does RFID Do for the Consumer?," Comm. of the ACM, Sep. 2005, vol. 48, No. 9, pp. 77-79.
Gunther et al., "RFID and the Perception of Control: The Consumer's View," Comm. of the ACM, Sep. 2005, vol. 48, No. 9, pp. 73-76.
Ohkubo et al., "RFID Privacy Issues and Technical Challenges," Comm. of the ACM, Sep. 2005, vol. 48, No. 9, pp. 66-71.
Hsi et al., "RFID Enhances Visitors' Museum Experience at the Exploratorium," Sep. 2005, vol. 48, No. 9, pp. 60-65.
Pering et al., "Spontaneous Marriages of Mobile Devices and Interactive Spaces," Sep. 2005, vol. 48, No. 9, pp. 53-59.
Sample et al., "Design of an RFID-Based Battery-Free Programmable Sensing Platform," IEEE Trans. on Instr. and Meas., vol. 57, No. 11, Nov. 2008, pp. 2608-2615.
Raskar et al., "Photosensing Wireless Tags for Geometric Procedures," Sep. 2005, vol. 48, No. 9, pp. 46-51.
Smith et al., "RFID-Based Techniques for Human-Activity Detection," Sep. 2005, vol. 48, No. 9, pp. 39-44.
Borriello, "RFID: Tagging the World," Sep. 2005, vol. 48, No. 9, pp. 34-37.
U.S. Appl. No. 11/941,367, filed May 21, 2009, Fay.
U.S. Appl. No. 12/273,014, filed Nov. 18, 2008, Bommer.

* cited by examiner

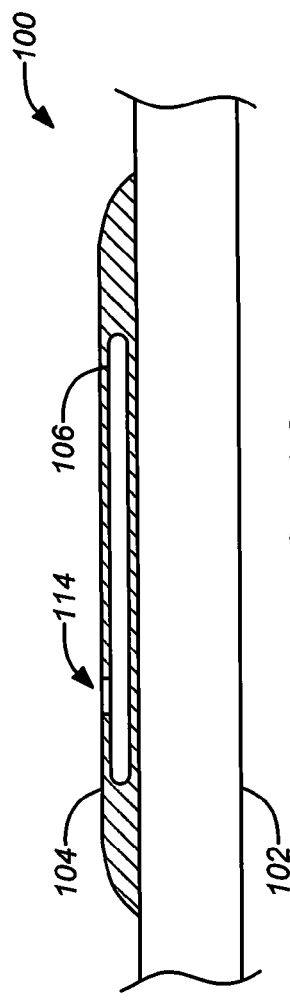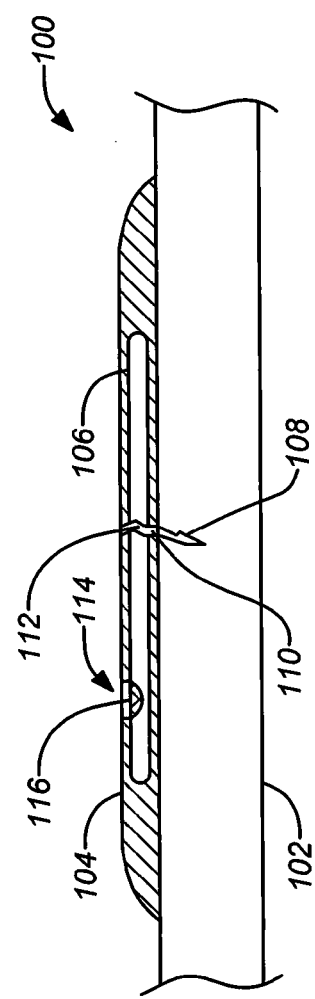
FIG. 1A
FIG. 1B

TRANSMISSION LINE MOISTURE SENSOR

CROSS-REFERENCE TO RELATED APPLICATIONS

This application is a Continuation-In-Part of the following co-pending and commonly-assigned U.S. utility patent applications, which are both incorporated by reference herein:

U.S. patent application Ser. No. 11/941,367, by Fay et al. filed Nov. 16, 2007, and entitled "CORROSION DETECTING STRUCTURAL HEALTH SENSOR" and U.S. patent application Ser. No. 12/273,014, by Bommer et al. filed Nov. 18, 2008, and entitled "RFID-BASED CORROSION AND MOISTURE DETECTION".

This application is related the following co-pending and commonly-assigned U.S. utility patent application, which is incorporated by reference herein:

U.S. patent application Ser. No. 12/202,883, by Fay et al. filed Sep. 2, 2008, and entitled "HYBRID RESILIENT AND FRANGIBLE LAYERED STRUCTURAL HEALTH SENSOR".

BACKGROUND OF THE INVENTION

1. Field of the Invention

This disclosure relates to structural testing. Particularly, this disclosure relates to techniques for monitoring potential corrosion of structural elements over time in service.

2. Description of the Related Art

The need to monitor the integrity of structural elements arises in many different applications. For example, it is necessary to monitor the structures of aircraft. The aircraft stay in service for many years and may experience environments that may exceed design limits resulting in different types of failures, e.g., fatigue, fracture, corosion. Therefore, it is necessary to regularly check the structural integrity of the vehicle as part of any prudent maintenance program. Similarly, other types of structures may also require regular monitoring. Highway structures such as overpasses and bridges must be regularly checked. Some building structures may also require regular testing. Conventional testing techniques such as visual inspection, x-ray, dye penetrant, and electrical field techniques (e.g. eddy current testing, etc.) for testing structural elements have many drawbacks.

Visual inspection of structural members often requires some degree of disassembly of the structure. This adds greatly to the overall testing cost. For example, visual inspection for aircraft structures requires substantial disassembly of structure and removal of installed equipment in order to provide the access needed to view the areas of interest at a distance adequate to detect corrosion visually.

X-Ray testing, under the broader heading of radiographic testing, requires specialized facilities and government licenses. The technique employs the ability of short wavelength electromagnetic radiation to penetrate various materials. Either an X-ray machine or a radioactive source can be used as a source of photons. Because the amount of radiation emerging from the opposite side of an examined material can be detected and measured, variations in the intensity of radiation are used to determine thickness or composition of material and reveal any defects. Due to safety issues, X-ray testing also typically requires a complete work stoppage on all other tasks while the testing is being performed.

Dye penetrant testing is also time consuming and messy. Dye penetrant inspection is used to reveal surface breaking flaws through the bleedout of a colored or fluorescent dye from the flaw. The technique is based on the ability of a liquid to be drawn into a surface breaking flaw by capillary action. After a period of time, excess surface penetrant is removed and a developer is applied. This acts as a blotter. It draws the penetrant from the flaw to reveal its presence. The consituent penetrant and developer may and their by-products may be identified as hazardous materials (HAZMAT), requiring costly disposal means.

Finally, inspection methods using the application of electrical fields (e.g., eddy current testing, etc.) are exceptionally time consuming and difficult to read reliably in this type of application and may require alterations to structure. In typical eddy current testing for example, a circular coil carrying an AC current is placed in close proximity to an electrically conductive specimen to be tested. The alternating current in the coil yields a changing magnetic field, which interacts with the test object and induces eddy currents in it. Variations in the phase and magnitude of these eddy currents can be monitored using a second coil, or by measuring changes to the current flowing in the primary coil. The presence of any flaws or variations in the electrical conductivity or magnetic permeability of the test object, will cause a change in eddy current flow and a corresponding change in the phase and amplitude of the measured current. The technique is generally limited to detecting surface breaks or near surface cracking and variations in material composition. In addition, a novel structural health sensor type has been recently developed employing a thin breakable conductor sense loop in a frangible membrane.

U.S. Pat. No. 7,621,193, by Fay et al. issued Nov. 16, 2007, and entitled "FRACTURE DETECTING STRUCTURAL HEALTH SENSOR" discloses a sensor device for monitoring and testing the integrity of structural elements. A frangible membrane including a thin breakable conductor sense loop is bonded to a structural element to be tested. A fracture in the bonded structural element induces a disruption in the both the frangible membrane and the thin breakable conductor sense loop. Measured electrical property change of the disrupted conductor sense loop reveals the fracture in the structural element. Connection to the sensor device may be through a connector or using a wireless reader which remotely energizes the sensor device. The sensor may also be implemented as a gasket and/or employ weep holes to the breakable conductor to reveal possible corrosion as well.

In view of the foregoing, there is a need in the art for apparatuses and methods for efficiently monitoring the integrity of structural elements. In particular, there is a need for such apparatuses and methods to monitor corrosion of structural elements without requiring time-consuming disassembly. There is also a need for such apparatuses to be light weight. And there is further a need for such apparatuses and methods to be inexpensive to implement and use. There is particularly a need for such systems and apparatuses in aircraft applications. These and other needs are met by the present disclosure as detailed hereafter.

SUMMARY OF THE INVENTION

A sensor device for monitoring and testing for potential corrosion of structural elements is disclosed comprising a soluble material disposed adjacent to at least one conductor in a transmission line that reacts to the presence of moisture causing a detectable change in an electrical property of the conductor. The conductor may comprise a conductive ink that is disrupted when the soluble material dissolves beneath it. Alternately, the nonconductive soluble membrane may separate two conductors and moisture causes a disruption in the soluble membrane allowing the two conductors to short. Detected changes in the electrical properties of the one or more conductors can be used to indicate potential corrosion or structural imparement in the structural element. Connection to the sensor device may be through a connector or using a wireless reader which remotely energizes the sensor device comprising one or more RFID chips. An exemplary transducer embodiment may be formed by applying electrical transmission lines or ports to a moisture sensitive material (e.g. poly vinyl alcohol (PVA)) to form a binary switch function in an RF communication or power link capable of passively reporting the state.

A typical embodiment comprises a first conductor and a soluble material disposed adjacent to the first conductor such that moisture dissolves the soluble material to induce a change in an electrical property of the first conductor detectable through a connecting device indicating a possible structural problem in a nearby structural element. Typically, the non-conductive soluble material may comprise polyvinyl alcohol (PVA) and is substantially non-conductive.

In some embodiments, the first conductor may comprise a conductive ink supported by the soluble material and the moisture dissolves the soluble material and thereby disrupts the conductive ink and thereby breaks continuity of the first conductor to induce the change in the electrical property. The first conductor may form an antenna for one or more RFID chips coupled thereto and disruption of the conductive ink induces a change in a wireless response signal from the one or more RFID chips as the change in the electrical property. The first conductor and the one or more RFID chips may be passive and powered through a wireless remote reader as the connecting device.

In further embodiments, a second conductor may be disposed adjacent to the first conductor. A differential compression load exists between the first conductor and the second conductor and the soluble material prevents electrical contact between the first conductor and the second conductor. The moisture dissolves the soluble material to allow contact between the first conductor and the second conductor to induce the change in the electrical property of the first conductor detectable through the connecting device indicating the possible structural problem in the nearby structural element. The first conductor, the second conductor and the soluble material may be disposed within a gasket having weep holes that allow the moisture to reach the soluble material. In addition, the first conductor and the second conductor may form an antenna for one or more RFID chips coupled thereto and contact between the first conductor and the second conductor induces a change in a wireless response signal from the one or more RFID chips as the change in the electrical property. The first conductor and the second conductor and the one or more RFID chips may be passive and powered through a wireless remote reader as the connecting device.

Using the conductive ink or the two conductors, the one or more RFID chips may comprise a first and a second RFID chip and contact between the first conductor and the second conductor toggles disconnecting the first RFID chip from the antenna and connecting the second RFID chip to the antenna. Alternately, the one or more RFID chips may comprise a single RFID chip and contact between the first conductor and the second conductor disconnects the single RFID chip from the antenna.

A typical method embodiment for sensing corrosion, comprises the steps of disposing a first conductor adjacent to a soluble material, dissolving the soluble material with moisture to induce a change in an electrical property of the first conductor, and detecting the change in the electrical property through a connecting device to indicate a possible structural problem in a nearby structural element. The method embodiment may be further modified consistent with the apparatus embodiments and systems described herein.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

Referring now to the drawings in which like reference numbers represent corresponding parts throughout:

FIG. 1A illustrates a side view of an exemplary membrane moisture sensor installed on a structural element;

FIG. 1B illustrates a side view of the exemplary membrane moisture sensor indicating a corrosion;

DETAILED DESCRIPTION OF THE PREFERRED EMBODIMENT

1. Overview

Figure 1C:
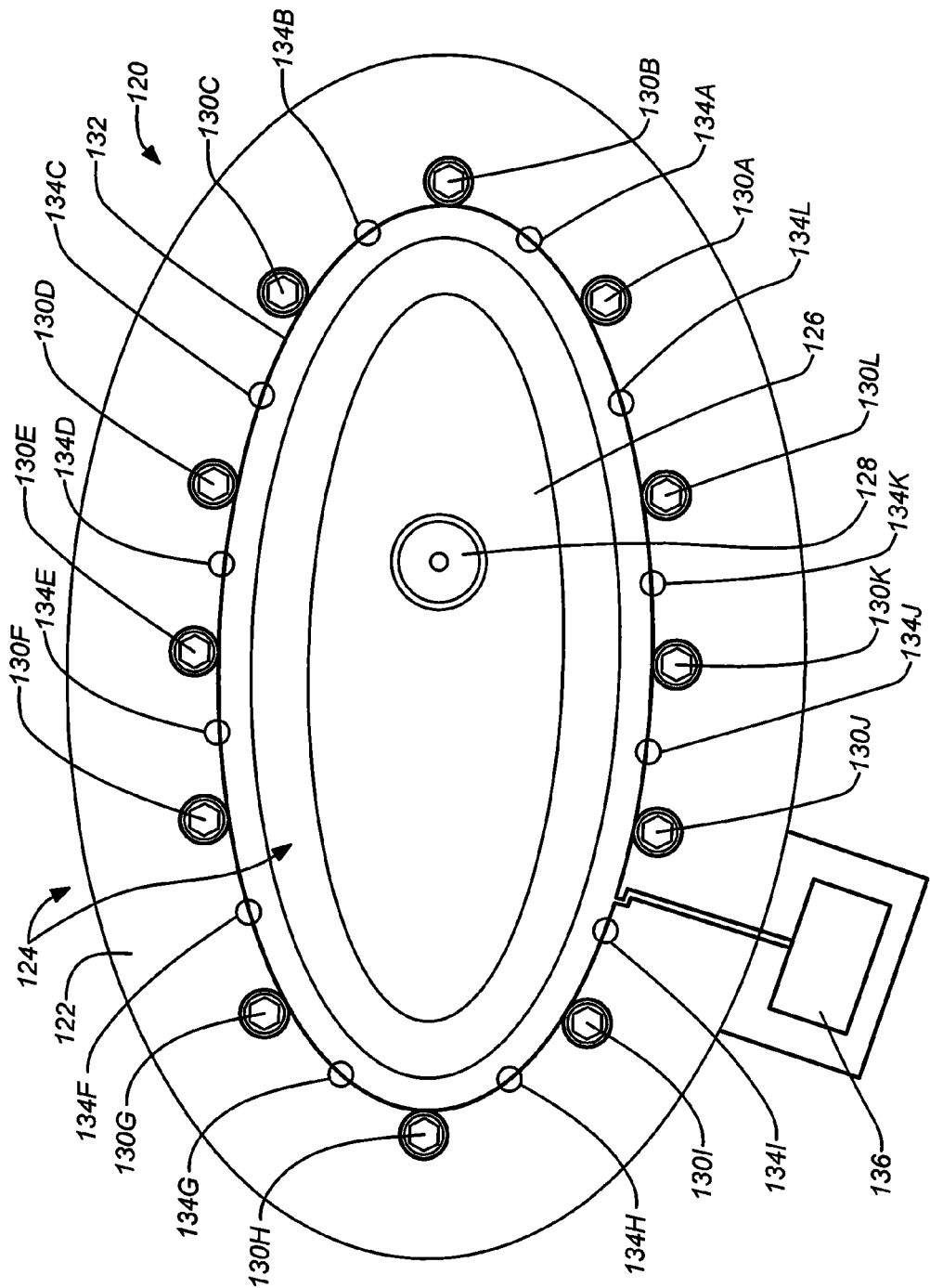
FIG. 1C illustrates a top view of an exemplary membrane moisture sensor.

As previously mentioned, a sensor device for monitoring and testing for potential corrosion of structural elements is disclosed comprising a transmission-line based transducer that reacts to the presence of moisture and may be used to enable a passive wireless communication of the change. A nonconductive soluble membrane separates two conductors disposed near a structural element to be monitored. Moisture causes a disruption in the soluble membrane allowing the two conductors to short. Detected changes in the electrical properties of the two conductors can be used to indicate potential corrosion or structural imparement in the structural element. Connection to the sensor device may be through a connector or using a wireless reader which remotely energizes the sensor device. An exemplary transducer embodiment may be formed by applying electrical transmission lines or ports to a moisture sensitive material to form a binary switch function in an RF communication or power link capable of passively reporting the state.

The unique and novel features of these transmission-line transducers include that they can be integrated well with extremely low operating power and large spatial sampling, making them suitable for wireless platforms and the targeted applications. The transducer can be formed by leveraging the multi-function characteristics of a soluble material backed transmission line. Since a transmission line is inherently required in the parent application, U.S. patent application Ser. No. 11/941,367, by Fay et al. filed Nov. 16, 2007, and entitled "CORROSION DETECTING STRUCTURAL HEALTH SENSOR", adding a soluble transmission line or strain-sensitive transmission line provides a cost effective method of sensing either of these failures at no additional circuit or transducer cost.

A corrosion sensor in accordance with an embodiment of the invention can lower the total cost of ownership for an aircraft or other vehicle based on the labor it can save and the additional equipment availability it can provide. Operators will not have to take equipment out of service, provided that there are no incidents of damage that need to be repaired. In contrast, conventional methods require copious labor and extended periods out of service to accomplish—even if no repairs are required. Conventional methods also enhance the risk of maintenance induced damage during the disassembly required for access.

Embodiments of the disclosure can be used to automatically detect the presence of an environment conducive to corrosion, which can enable the replacement of time-consuming visual inspection procedures with a much simpler and quicker nonintrusive inspection. Embodiments of the disclosure can take advantage of known radio frequency identification (RFID) technology to yield a passive and wireless interface for a sensor system. Such a system can be particularly useful in corrosion monitoring of aircraft, although embodiments of the disclosure are not limited to such applications. In some embodiments of the disclosure, conventional RFID technology can be applied to create a binary detector, capable of sensing moisture. The RFID-based corrosion and moisture detection techniques herein may be more generally described as RFID-based environmental structural sensing techniques.

Embodiments of the disclosure can enable inspections which do not require direct access to the structure. Using embodiments of the disclosure, periodic visual inspections will no longer be required, thereby reducing time for disassembly and reassembly. These periodic inspections can be replaced with wireless inspections performed by a technician using a handheld scanner on short scheduled intervals (e.g., between flights). Thus, embodiments of the disclosure can enable inspections that can be performed rapidly with one person walking through the airplane with a handheld reader. The sensing technique is nonintrusive so the risk of damaging components during inspection is eliminated. Also, by varying the spacing of the sensors, almost any desired sensing resolution can be achieved. In addition, the sensors may be passive, not requiring a wired power source or battery. Another advantage of this system is that it does not require x-rays or other harmful radiation to function. The sensors may be powered wirelessly by the handheld reader. The sensors may not interfere with the existing form, fit, and function of the structure.

While other conventional corrosion sensors are commercially available, none are compatible with the example embodiment of the disclosure employed between structural surfaces. Existing corrosion sensors are not designed to the appropriate form factor to detect moisture or corrosion between the faying surfaces of an aircraft floor beam and floor panel. However, conventional corrosion sensors, as well as other types of structural sensor, may be implemented in other embodiments of the disclosure as will be understood by those skilled in the art. Although many embodiments described herein are directed to corrosion sensing in a structural joint, embodiments of the disclosure are not limited to corrosion sensing between faying surfaces of a structure. Furthermore, embodiments of the disclosure may be applied to any structure requiring regular inspections, e.g. aircraft, ships, automobiles, or buildings.

Embodiments of the disclosure employ structural health sensors uniquely adapted to operate with known passive wireless RFID technology as described hereafter. As used in the present application, a "structural health sensor" is a sensor that is disposed on a structural element and is triggered by the presence of a "structural problem indicator," a particular anomaly it detects according to its design that indicates there may be a problem that could negatively affect the structural element. Thus, the structural problem indicator may also be considered an event requiring structural inspection. Such sensors may be applied to any structural element, e.g. an aircraft bulkhead, or a bridge beam, to monitor its condition. The applicable structural problem indicator depends upon the particular type and design of the structural health sensor. For example, different types of structural health sensors may monitor for moisture or fractures. However, embodiments of the present disclosure are directed to corrosion structural health sensors for detecting a structural problem indicator of moisture presence. It should be noted that monitoring the "health" of a structure as used in the present application generally refers to employing any appropriate sensor for detecting any adverse condition (or the possibility of an adverse condition) of a structural element of interest.

2. Membrane Moisture Sensor

FIG. 1A illustrates a side view of an exemplary moisture membrane sensor 100 installed on a structural element 102. The corrosion sensor 100 comprises a membrane material 104 formed into a thin flat structure that may be disposed adjacent to the surface of a structural element 102. Typically the membrane material is bonded to the structural element. A conductor sense loop 106 is embedded within the membrane material 104. The membrane material 104 includes one or more weep holes 114 which penetrate to expose the conductor sense loop 106. For corrosion sensing, the membrane material need only support the conductor sense loop 106; it may be rigid or soft, although a resilient material is preferred to make the sensor 100 more durable. The exposed portion of the conductor sense loop 106 is used to sense corrosion as described with respect to FIG. 1B.

FIG. 1B illustrates a side view of the exemplary moisture corrosion sensor 100 indicating corrosion using one or more weep holes 114. Corrosion that develops on the portion of the conductor sense loop 106 exposed by the weep holes 114 in the membrane material 104 effects electrical properties of the conductor sense loop 106. The change in the electrical properties of the conductor sense loop 106 (e.g., resistance, inductance, capacitance or an open circuit indicating corrosion) can then be measured to sense the corrosion. The particular measured electrical property may be varied depending upon the application. In one example implementation, the membrane may be constructed from two layers of thin plastic film which contains the one or more fine wire sense loops sandwiched between. The membrane is a non-conductive material that is self adhesive at installation and effectively seals and protects the underlying structure from corrosion.

For example, the conductor material may be selected to be particularly susceptible to corrosion so that any moisture that comes in contact with the area will enter the weep hole 114 and cause at least a partial reduction of the exposed portion of the breakable conductor sense loop 106. This will result in an increase in the effective resistance of the conductor as the cross sectional area of the conductor is reduced by the corrosion. Thus, although actual corrosion of the structural element 102 may not yet exist, the weep hole 114 allows the conductor sense loop 106 to provide an early warning of possible corrosion to the structural element due to the presence of moisture. It should be noted that design of the conductor sense loop 106 may be optimized such that the portions of the conductor sense loop 106 may be treated differently or comprise a different material than the unexposed portions of the conductor sense loop 106 to enhance the corrosion sensitivity in this area. The ends of the conductor sense loop 106 are connected to a connecting device which is coupled to a sensing circuit that detects the corrosion (or optionally, fractures as well) as illustrated in the following FIG. 1C.

The membrane material should be non-porous. The membrane material should be both an effective electrical insulator and flexible enough to permit ease of installation. The membrane material should have good shelf-life qualities to permit stocking of spares. The membrane material must be non-corrosive. The membrane material and conductor sense loop material and size and selected electrical measurement parameters may be tailored to a specific installation application in order to maximize gasket and sensing performance as will be understood by those skilled in the art. Materials for the frangible membrane may have characteristics similar to paint coatings in appearance and include, but are not limited to polycarbonate, urethane, polyurethane, enamel, polyester, acrylic, epoxy, and a wide variety of plastics and other similar materials.

In addition to corrosion sensing, the sensor 100 may also be further adapted to detect other structural defects occurring in the adjacent structural element 102. To do this however, the conductor sense loop 106 of the corrosion sensor 100 must also be breakable conductor sense loop 106 and the membrane material must be frangible. The frangible membrane material 104 must be non-conductive so as not to short the breakable conductor sense loop 106 which is employed to detect a fracture or other structural failure in the surface of the structural element 102. In this case, a fracture 108 appearing in the surface of the structural element 102 induces a break 110 in the frangible material 104 which in turn carries through to cause a break 112 in the breakable conductor sense loop 106.

FIG. 1C illustrates a top view of an exemplary membrane moisture sensor 120. In this example, the membrane 122 is applied to the surface of a structural element 124 that is the metal skin of an aircraft at a location that has an antenna base 126 mounted. The airfoil 126 carries the antenna connector 128 within it and is bolted to the aircraft skin (structural element 124) by a series of bolts 130A-130L around the perimeter of the antenna base 126. The conductor sense loop 132 is embedded within the membrane 122 as previously described. Multiple weep holes 134A-134L at various locations along the conductor sense loop 132 permit one or more exposed portions of the conductor sense loop 132 to corrode as previously described to provide an early warning of potential corrosion to nearby structural elements.

The conductor sense loop 132 of the sensor 120 is coupled to a connecting device 136 which is used to connect to a reader device that measures changes in the electrical properties of the conductor sense loop 132. In the simplest implementation, the connecting device 135 may comprise a simple electrical connector. However, the connecting device 135 may also comprise a wireless communication tag as described hereafter which affords many advantages beyond a simple electrical connector. The reader device can be any known device capable of measuring the electrical properties of the conductor sense loop 132. The wireless communication tag incorporates some of the reader device with the tag.

The membrane 122 may be installed at structural locations where corrosion is a concern. At appropriate intervals, an operator uses a reader device to energize and read the membrane sensor 120. Either a wireless reader device or another external device may be used to compare the readings of a conductor sense loop to those of a reference value measured at each specific installation to determine if corrosion or damage is present. The reference value can be determined when the membrane or gasket sensor is designed for a specific application and manufactured. The reference value for the specific application can either exist in written form for manual measurement and analysis or be loaded into the wireless reader for automatic analysis.

In another example implementation, the sensor comprises a membrane material that is frangible after installation to also provide sensing of fractures or other structural failures in the underlying structural element. In this case, the objective is that the composition of the frangible membrane should match the structure material it is bonded to such that if a crack occurs in the structural element, the frangible membrane cracks as well, breaking (or otherwise disrupting) the conductor which forms the sense loop. For fracture detection, the conductor sense loop 132 is generally position transversely across locations where a fracture is most likely. For example, in FIG. 1C the conductor sense loop 132 takes a route around the perimeter of the antenna airfoil 126 where any structural failures are likely to appear. In a like manner, the conductor sense loop 132 is routed around each of the bolts 130A-130L in small loops.

The frangible membrane may be either a pre-formed device or fabricated on site. The frangible membrane material should be an effective electrical insulator and flexible enough prior to installation to permit ease of installation. The frangible membrane material should have good shelf-life quality to permit stocking of spares. The frangible membrane material must be non-corrosive, particularly to the breakable conductor sense loop. The frangible membrane and sense loop materials and sizes and electrical measurement characteristics can be selected for a specific installation to maximize membrane performance. Materials for the frangible membrane may have characteristics similar to paint coatings in appearance and include, but are not limited to polycarbonate, urethane, polyurethane, enamel, polyester, acrylic, epoxy, and a wide variety of plastics and other similar materials.

The sense loop may be custom tailored to the specific application. It can typically be constructed from the same material (e.g., base metal and alloy) as the structural element at the installed interface. The configuration and size of the sense loop should be appropriate to ensure the conductor breaks when and if the membrane fractures. Materials for the sense loop include, but are not limited to aluminum, steel, copper, magnesium, titanium, and other similar materials. A membrane sensor device may also be implemented in a gasket configuration as described in the next section.

3. Gasket Moisture Sensor

Figure 2A:
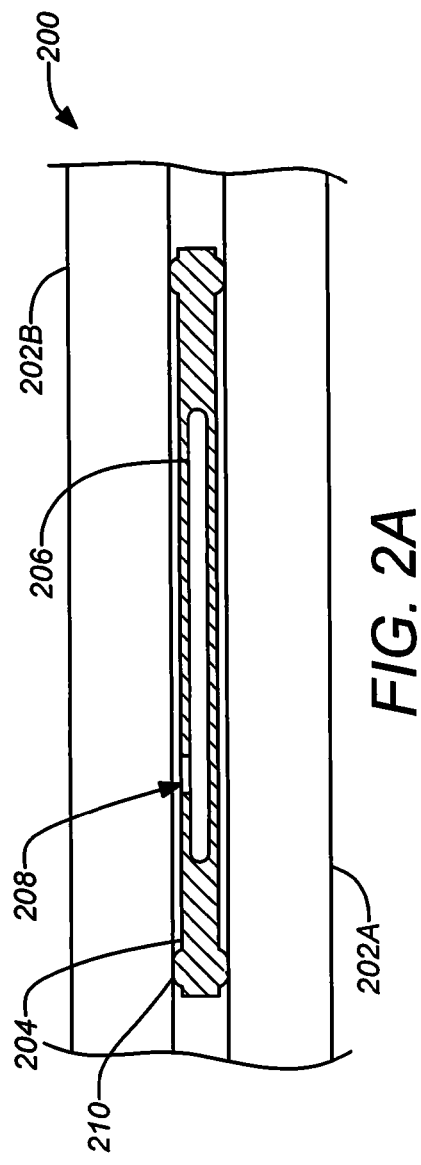
FIG. 2A illustrates a side view of an exemplary moisture sensor in a gasket configuration.

FIG. 2A illustrates a side view of an exemplary membrane moisture sensor 200 in a gasket. The sensor 200 comprises a membrane material 204 formed into a thin flat structure that is disposed adjacent to the surfaces of two structural elements 202A, 202B. In this case, the membrane material is sandwiched between the structural elements 202A, 202B. A conductor sense loop 206 is embedded within the membrane material 204. Here also, the membrane material 204 must be non-conductive so as not to short the conductor sense loop 206 employed to detect potential corrosion of either of the structural elements 202A, 202B. The membrane material 204 includes one or more weep holes 208 which penetrate to expose the conductor sense loop 206. The conductor sense loop 206 is used to provide early detection of corrosion as previously described. The gasket configuration of the sensor 200 can also include one or more ribs 210 built into one or both sides of the frangible material 204. The ribs 210 are designed to provide a seal against one or both surfaces of the structural elements 202A, 202B.

Figure 2B:
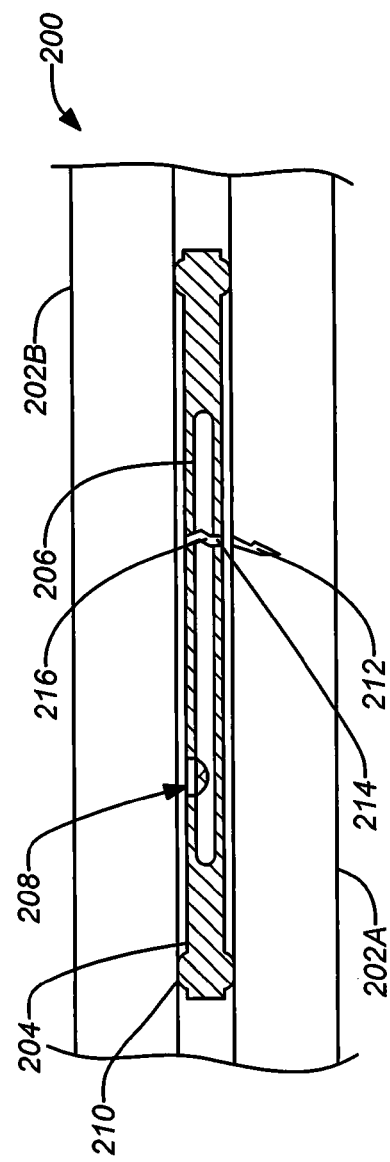
FIG. 2B illustrates a side view of an exemplary moisture sensor in a gasket indicating corrosion.

FIG. 2B illustrates a side view of the exemplary membrane moisture sensor 200 in a gasket indicating corrosion. As previously described, the conductor material may be selected to be susceptible to corrosion so that any moisture that comes in contact with the area will enter the weep hole 208 and cause at least a partial erosion of the conductor. For example, this may be used to cause an increase in the effective resistance of the conductor as the cross sectional area of the conductor is reduced by the corrosion. Thus, although actual corrosion of the structural elements 202A, 202B may not exist yet, the weep hole 208 allows the conductor sense loop 206 to provide an early warning of possible corrosion to either structural element 202A, 202B due to the presence of moisture.

It should be noted that the gasket configuration is particularly well suited for early corrosion detection because the both surfaces of the membrane material 204 are intended to remain sealed from the environment (with or without the sealing ribs 210). Thus, any moisture present in the weep holes 208 would not be evident even under a visual inspection. Finally, the ends of the conductor sense loop 106 are connected to a connecting device which is coupled to a sensing circuit that detects the corrosion.

If fracture sensing is also desired, the membrane material 204 must also be frangible and the conductor sense loop 206 breakable as previously described. A fracture 212 appearing in the surface of at least one structural element 202A induces a break 214 in the frangible material 204 which in turn carries through to cause a break 216 in the breakable conductor sense loop 206. Corrosion that develops in the weep holes 208 in the frangible material 204 may cause a break in the breakable conductor sense loop 206 as well.

Figure 2C:
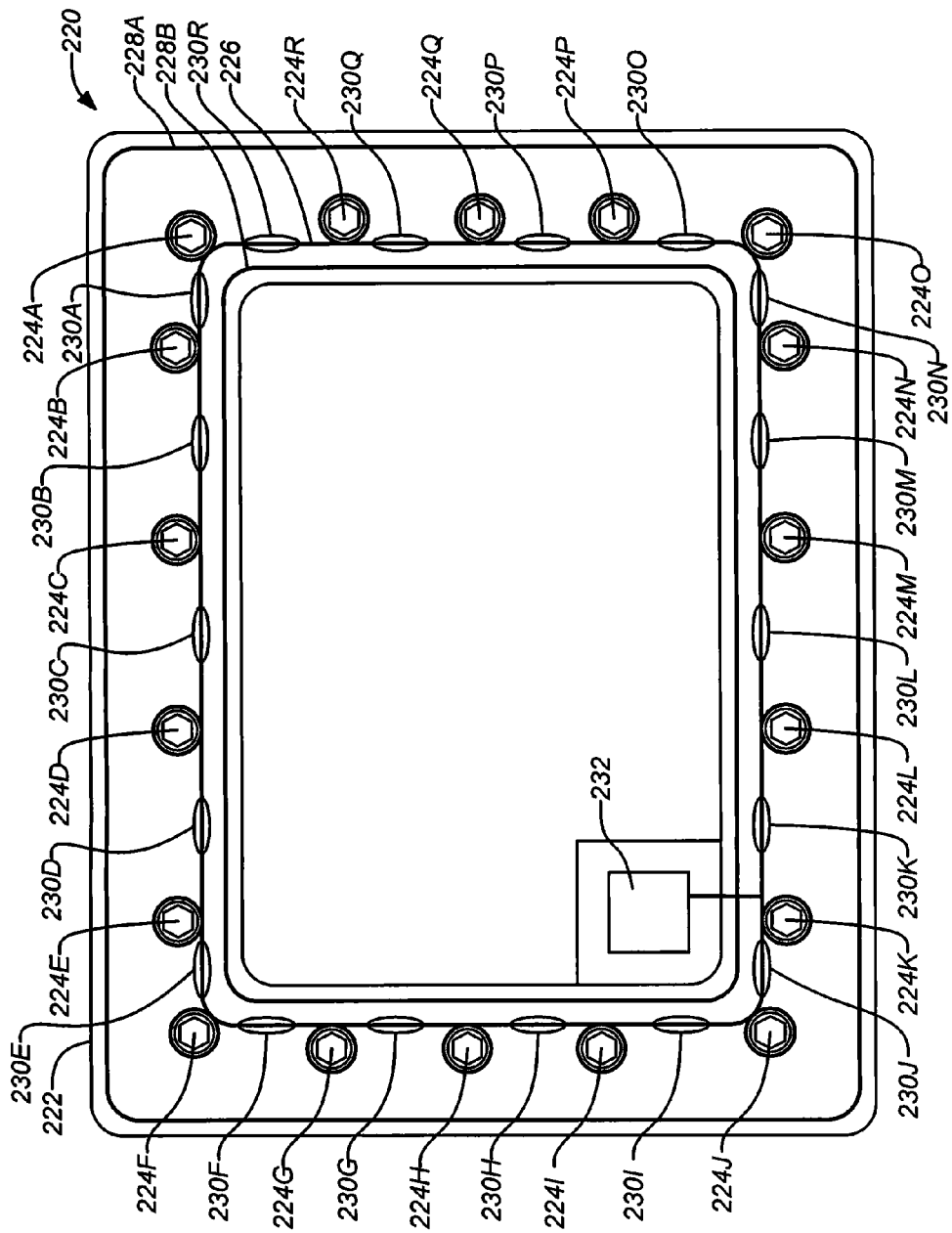
FIG. 2C illustrates a top view of an exemplary moisture sensor in a gasket configuration.

FIG. 2C illustrates a top view of an exemplary membrane moisture sensor 220 in a gasket. Communication with the sensor 220 may be accomplished using any known technique. In this configuration, a membrane 222 is sandwiched between the surfaces of two structural elements as described in FIGS. 2A and 2B. For example, the structural elements may be a joint between two components of an aircraft. A series of bolts 224A-224R are disposed around the interface between the structural elements. The conductor sense loop 226 is embedded within the membrane 222 as previously described and is routed around the interface as well. Weep holes 230A-230R at various locations along the breakable conductor sense loop 226 which operate as previously described to provide an early warning of potential corrosion. Ribs 228A, 228B are also laid out around the perimeter of both the inner and outer edges of the gasket membrane 222 (on one or both sides of the membrane as previously described in FIGS. 2A and 2B) to seal the membrane surface and the structural element surfaces from moisture.

The conductor sense loop 226 of the gasket sensor 220 is coupled to a connecting device 232 which is used to connect to a reader device that measures changes in the electrical properties of the conductor sense loop 226 indicating corrosion. The reader device can be any known device capable of measuring the electrical properties of the conductor sense loop 226. In a simple implementation, the connecting device 232 may comprise an electrical connector. However, the connecting device 232 may also comprise a wireless communication tag as described in the next section which affords many advantages beyond a simple electrical connector. The wireless communication tag incorporates some of the reader device with the tag.

The gasket may be installed at structural interfaces where corrosion inspections were previously scheduled, or areas of interest. The gasket remains installed serving to seal the interface against the intrusion of liquids and other contaminants. The gasket is entirely benign in its installed environment with respect to corrosion and emitted energy. At appropriate intervals, the operator uses a wireless reader device to energize and read the gasket. Either a wireless reader or another external device will compare the readings of the one or more conductor sense loops to those of the reference value measured at each specific installation to determine if corrosion or damage is present. The reference value can be determined when the membrane or gasket sensor is designed for a specific application and manufactured. The reference value for the specific application can either exist in written form for manual measurement and analysis or be loaded into the wireless reader for automatic analysis.

The gasket may be designed to form an effective seal for the faying surface of the joint in order to mechanically prevent liquids from intruding. The gasket material should be non-porous and resilient (i.e., returns to original shape after becoming deformed by applied pressure) over several inspection intervals. The gasket material should be both an effective electrical insulator and flexible enough to permit ease of installation. The gasket material should have good shelf-life qualities to permit stocking of spares. The gasket material must be non-corrosive. The gasket material and conductor sense loop material and size and selected electrical measurement parameters may be tailored to a specific installation application in order to maximize gasket and sensing performance. Materials for the gasket include, but are not limited to silicone, rubber, nitrile, Buna-N, neoprene, Teflon, and other similar materials.

The sensor 220 may also be used for fracture detection using a frangible membrane and breakable conductor sense loop 226 in combination with corrosion sensing. In this case, the breakable conductor sense loop 226 should be laid perpendicular to where any structural failures are likely to appear. Thus, the breakable conductor sense loop 226 is routed around each of the bolts 224A-224R in small loops.

There are two critical parameters which drive the electrical and mechanical designs for the moisture sensing system. The first is the available space between the floor panel and the substructure (i.e. floor beam, seat track, intercostal). The available space may be estimated to be in the range of $1/32$ to $3/16$ inches. Moreover, to prevent moisture ingression in the faying surface, it is common to line the entire surface with a moisture sealing tape, e.g. SkyFlex, which doubles as a noise damper. The other critical parameter to consider, especially in the electrical design, is the conductivity of the substructure and floor panel. It may be conservatively assumed that the floor panel and substructure are both highly conductive. Thus, the moisture sensor must be operable in a very small space between what are effectively two electrically conducting plates.

With the maximum thickness defined the electrical components of the device can be constrained to an outer hard shell, or gasket, which provides protection to these components and may be integrated into a multi-functional design such as a moisture or acoustic grade tape. The gasket can include several form factors of varying dimensions to accommodate a wide range of faying surfaces. Also included on the gasket may be varying arrangements of weep holes designed to promote ingression of moisture into the sensing element in the case that the sealing function of the gasket fails.

4. Transmission Line Moisture Sensor

Embodiments of the present disclosure are directed to a novel moisture sensing mechanism that may be employed within any either a a membrane or gasket configuration, e.g. as described in FIGS. 1A-2C of the previous section. However, in this case at least a portion of the conductive element, e.g. the conductor sense loop 106, 132, 206 or 226, includes at least one conductor that is adjacent to a nonconductive soluble material such that when the soluble material dissolves a detectable change in an electrical property of the conductor occurs to indicate a possible structural problem in a nearby structural element. In one example, the conductor may comprise a conductive ink disposed on a soluble material. In another example, a two-wire sensor with a separating soluble material may be used.

Figure 3A:
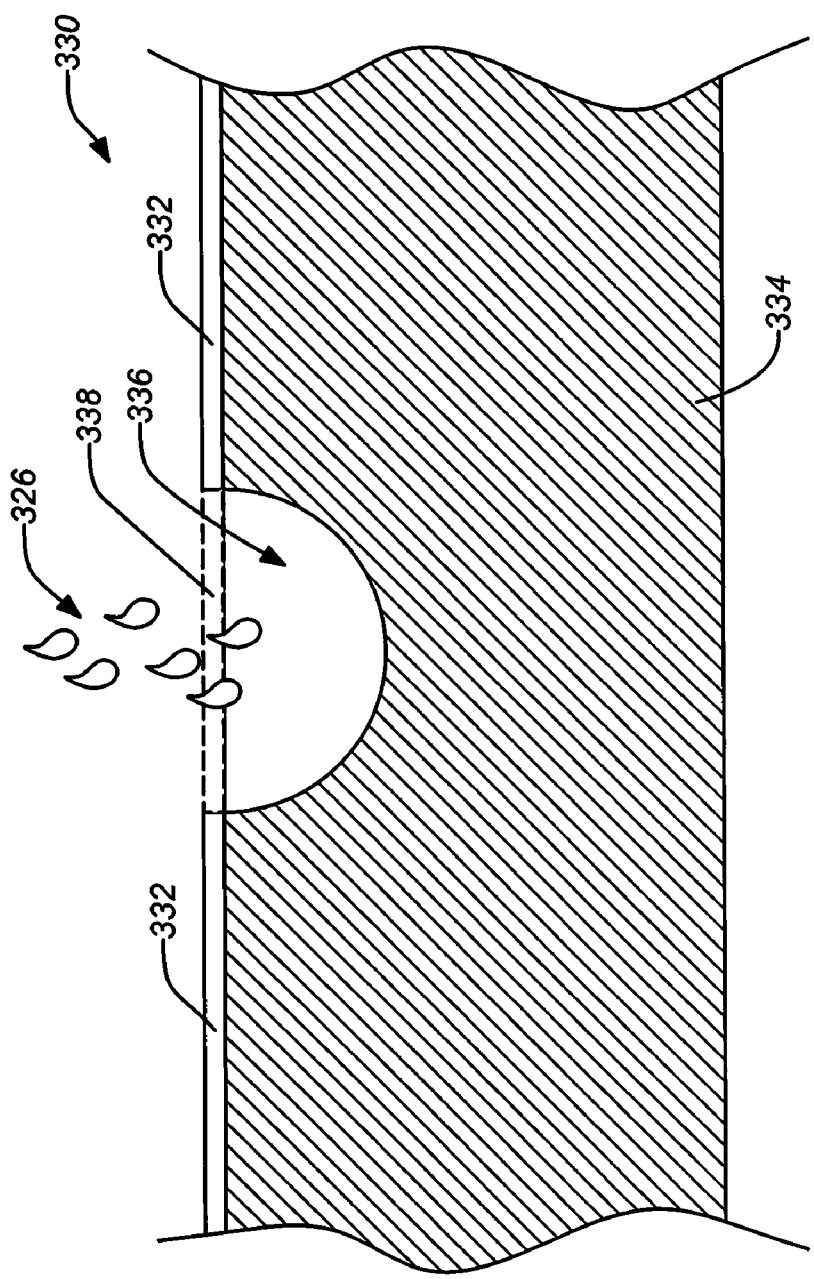
FIG. 3A illustrates a conductive ink moisture sensor.

FIG. 3A illustrates a conductive ink moisture sensor 330 that operates as a moisture sensor and switch mechanism. In this sensor 330, a first conductor 332 comprises a conductive ink that is applied to a surface of soluble material 334. The conductive ink is applied in a relatively thin layer such that when moisture 326 contacts the soluble material 334, it dissolves at least a portion of the soluble material 334 in an region 336 beneath the soluble ink which causes a disruption in overlying portion 338 of the first conductor 332 which will be detectable as a break (or lesser impedance change) in the circuit of the first conductor 332.

Figure 3B:
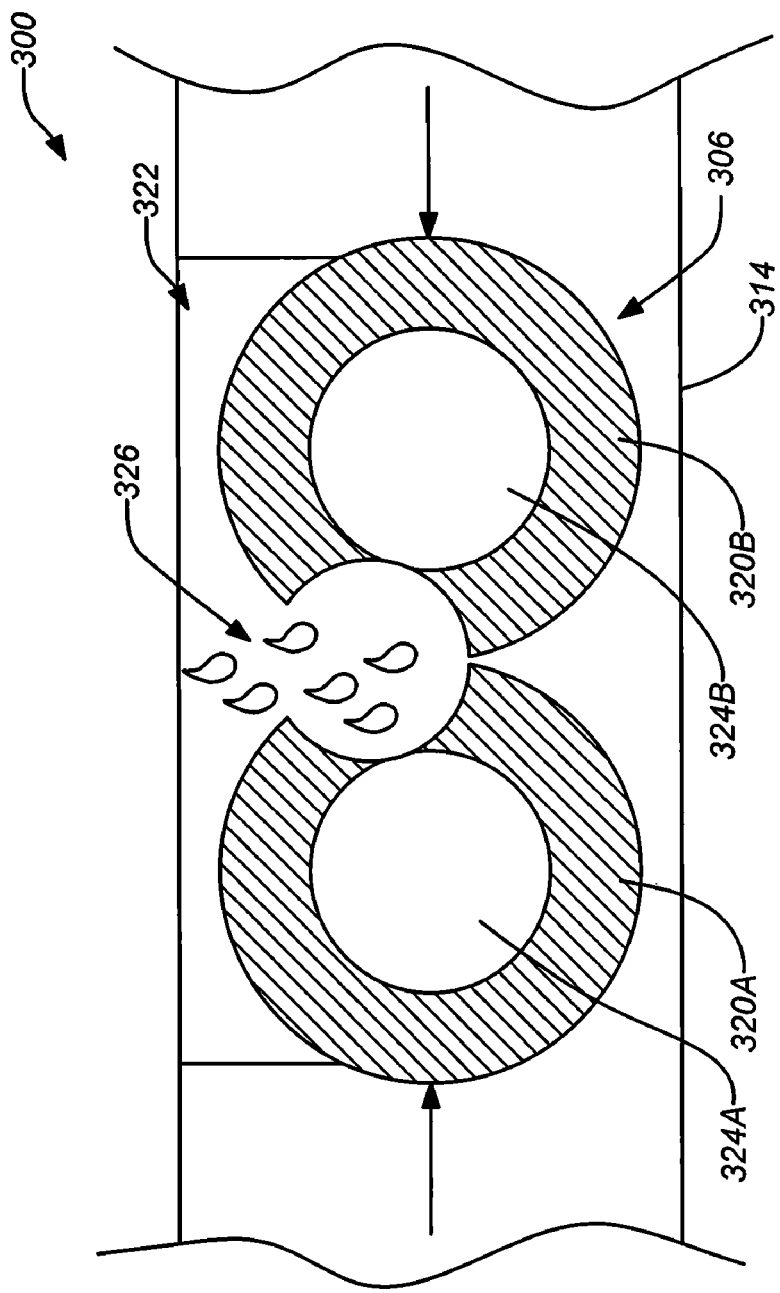
FIG. 3B illustrates a two-wire moisture sensor.

FIG. 3B illustrates an alternate two-wire moisture sensor and switch mechanism in a moisture sensor device 300. The transmission line structural health sensor 306 comprises a two-wire line having a soluble shield 320A, 320B around each of the wires 324A, 324B at multiple locations along its length within the layer 314. In one example, the soluble shield 320A, 320B may be constructed from a polyvinyl alcohol (PVA) water soluble film or any other suitable water soluble material. The presence of moisture 326 (e.g. contacting the sensor 304 through weep hole 322) dissolves the shield 320A, 320B bringing two conductive wires 324A, 324B of the sensor 306 in contact in a short circuit, terminating communication with the RFID chip. The wires 324A, 324B should be loaded in compression (indicated by the arrows) to facilitate ready contact between the wires 324A, 324B as the shields 320A, 320B dissolve. Although it is preferable that the wires 324A, 324B contact each other causing a short, small impedance changes should also be detectable in the presence of moisture 326 before fully shorting.

One example soluble material that may be used for the moisture sensitive transducer is polyvinyl alcohol (PVA, also known as PVOH or PVAL) from a company, Sekisui Specialty Chemicals America, LLC. Sekisui produces and sells PVA in two main product lines, Celvol (an additive in paper, textiles, ceramics) and Premiol (a petroleum additive used for chemical stabilization). Another manufacturer, Aicello, also produces a water soluble film derived from PVA, called Solublon. This PVA is typically used in applications such as packaging, mold release, transfer printing, embroidery, medical and textiles (http://www.solublon.com/).

PVA has a range of possible solubilities which can be selected to tailor a particular moisture transducer. As described hereafter, the transducer changes state when this material is dissolved in the presence of moisture. The desired properties of the PVA can be tuned for a particular sensor application. In general, the PVA properties vary with changes in the degree of hydrolysis and molecular weight of the PVA. For example, increasing solubility results from decreasing molecular weight and/or solubility of the PVA, while increasing block resistance results from increasing molecular weight and/or solubility of the PVA. Although the present invention is described using PVA as the soluble material, those skilled in the art will appreciate that other known soluble materials may be selected having appropriate properties to function consistent with the principles of the defined embodiments described herein.

Figure 3C:
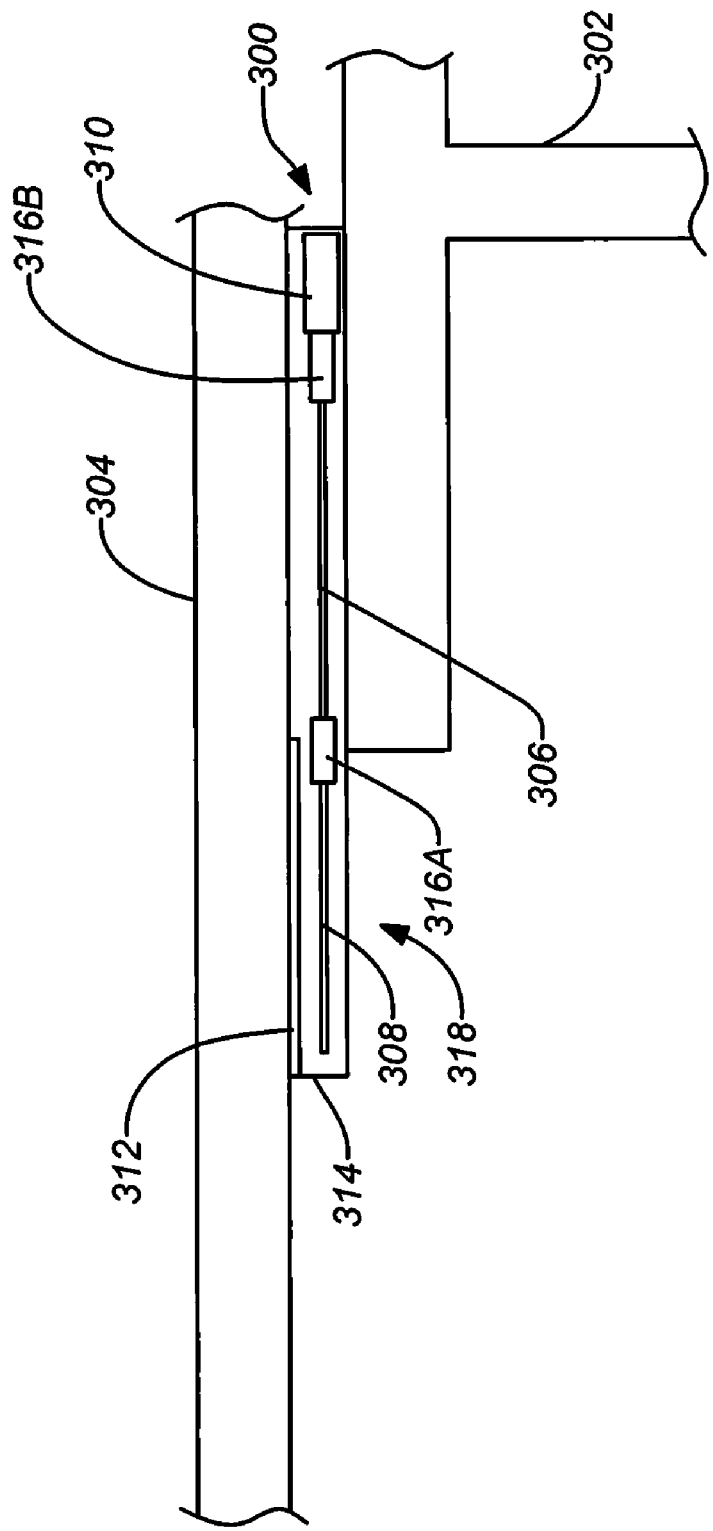
FIG. 3C illustrates an exemplary structural health sensor device for moisture sensing.

FIG. 3C illustrates an exemplary structural health sensor 306 for moisture sensing. This sensor device 300 is shown in a mechanical joint between a metal beam 302 and a metal panel 304. The sensor device 300 comprises a nonconductive membrane layer 314 employing a particular structural health sensor 306 comprising a differential transmission line for moisture detection over an expanded region which increasing the likelihood that moisture anywhere present in the mechanical joint will be detected. The antenna 308 (e.g., a conductive ink or a two-wire antenna) is disposed in a region 318 outside the mechanical joint and is coupled to the structural health sensor 306 which is in turn coupled to an RFID chip 310. A dielectric material layer 312 (having a quarter wavelength thickness, e.g. for 2.4 GHz) for the antenna 308 may be used to prevent any interference from the conductive panel 304. In this example sensor device 300, matching sections 316A, 316B are used to couple the differential transmission line structural health sensor 306 to both the RFID chip 310 at one end and the antenna 308 at the other. As is known in the art, a traditional RFID tag has a chip and antenna that each exhibit a characteristic impedance. In order to communicate through the antenna 308, the RFID chip 310 must be impedance matched to the antenna 308 so that signal reflections at the interface are minimized. Introducing a transmission line or switch, causes the impedance to change. Therefore, impedance matching elements should be introduced at the interfaces to optimize performance.

Figure 3D:
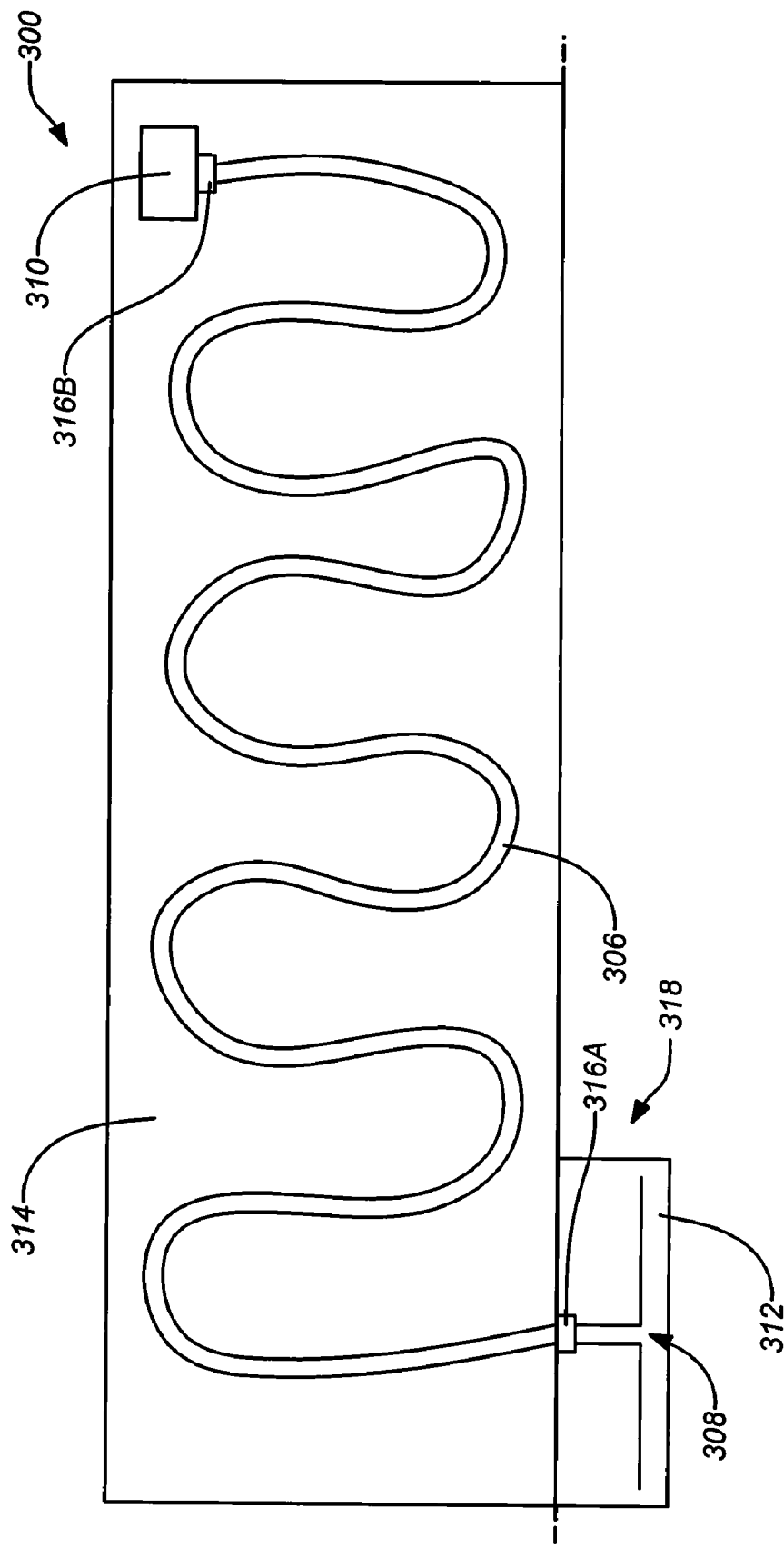
FIG. 3D illustrates a top view of the exemplary structural health sensor for moisture sensing.

FIG. 3D illustrates a top view of the exemplary structural health sensor device 300 for moisture sensing. The matched antenna 308 and transmission line structural health sensor 306 enables communication and power to the RFID chip 310 from a remote reader (not shown). In addition, weep holes in the membrane layer 314 can be used allow moisture to enter and make contact with the transmission line structural health sensor 304. The novel transmission line structural health sensor 304 incorporates the switching function along its entire length as described in FIG. 3A. Accordingly, the transmission line structural health sensor 306 is routed along a path (e.g., a meanderline) within the membrane layer to any area desired to be monitored for moisture. Thus, the transmission line structural health sensor 306 comprises a plurality of switches for disconnecting the antenna effectively in parallel connection along the length of the transmission line.

5. RFID Chips in a Structural Health Sensor System

Figure 4A:
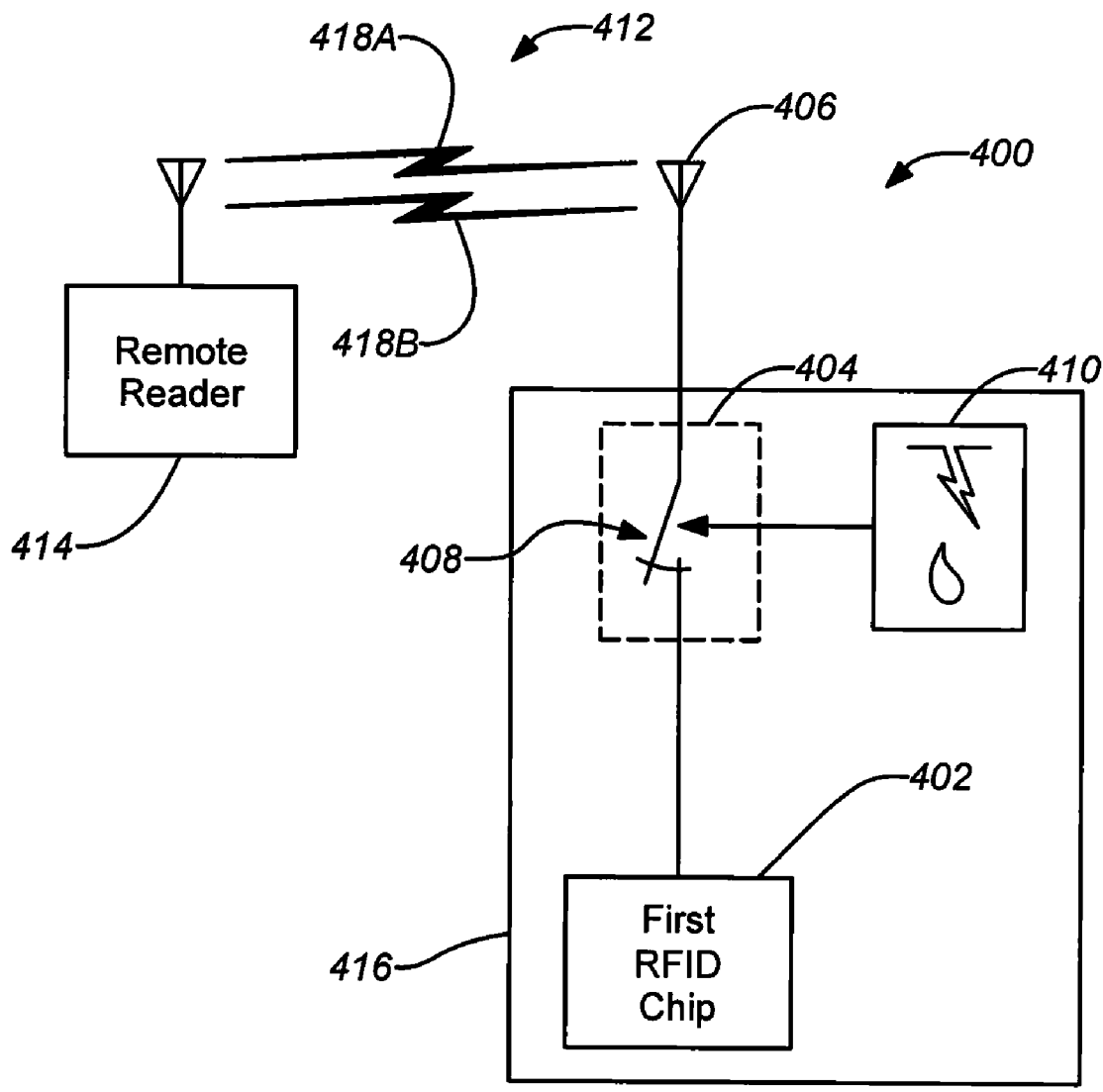
FIG. 4A is a schematic diagram of an exemplary embodiment for structural health sensing employing a single RFID chip.

FIG. 4A is a schematic diagram of an exemplary embodiment for structural health sensing employing a single RFID chip 402. The structural health sensing system 400 employs a first RFID chip 402 that is coupled to an antenna 406 through a structural health sensor 404. (Note that the RFID chip 402 is referenced as "first" in relation to further embodiments described hereafter employing more that one RFID chips.) The structural health sensor 404 includes a switch 408 capable of disconnecting the antenna 406 from the RFID chip 402 in response to a structural problem indicator 410. The applicable structural problem indicator 410 depends upon the particular type and design of the structural health sensor 404 which monitors the nearby structure 416. In one notable example, the structural health sensor 104 is designed to detect and respond to the presence of moisture. Thus, moisture is the structural problem indicator 410 for this example structural health sensor 404 which operates as previously described in FIGS. 3A-3C.

Monitoring of the structural health sensor 404 is performed through wireless communication 412. One important feature is the use of conventional RFID technology which employs passive electronics in the RFID chip 402. As is known in the art, the RFID chip 402 operates requiring minimal power which it receives through the wireless communication 412 link from the remote reader 414. The structural health sensor 404 employed in the system is similarly designed as a passive device that either requires no power or minimal power derived through the same wireless communication 412 link from the remote reader 414.

The remote reader 408 establishes the wireless communication 412 with the first RFID chip 402 through the antenna 406 when it is connected through the switch 408 of the sensor 404. Wireless communication 412 is typically established by the remote reader 414 first transmitting a query signal 418A to the RFID chip 402 through the antenna 406 and then receiving a response signal 418B from the RFID chip 402 through the antenna 406. In the system 400 of FIG. 4A, monitoring the structural health is possible because disconnecting the antenna 406 in response the structural problem indicator 410 prevents the response signal 418B from the first RFID chip 402 from being transmitted. Thus, receiving the response signal 418B at the remote reader 414 indicates structural health, but the remote reader 414 infers the presence of the structural problem indicator 410 from the absence of the response signal 418B after sending the query signal 418A.

As described in the example of FIG. 4A, a single sensor and RFID chip can be integrated with the antenna of the tag to create a binary state transponder. This implementation operates in a manner similar to RFID chips used in electronic article surveillance for consumer product theft prevention. The sensor is integrated into a portion of the antenna. In a healthy state the sensor is benign, leaving the connection to the antenna uncompromised and properly matched with the RFID chip. Thus, a query from a remote reader will be received and the RFID chip will properly respond. In the presence of corrosion or moisture, however, the sensor will degrade and may eventually break the conductive path causing a mismatch between the antenna and RFID chip. Such a mismatch will prevent communication between the reader and the RFID chip. Thus, moisture or corrosion is indicated by the lack of a response at the remote reader.

System 400 of FIG. 4A provides a significant improvement over the existing visual inspection method as it stands. The principle of this basic system 400 can be evolved to a higher sophistication level. One enhancement can be achieved by combining two RFID chips in one inlay with the sensor acting as a single pole double throw (SPDT) switch described hereafter.

Figure 4B:
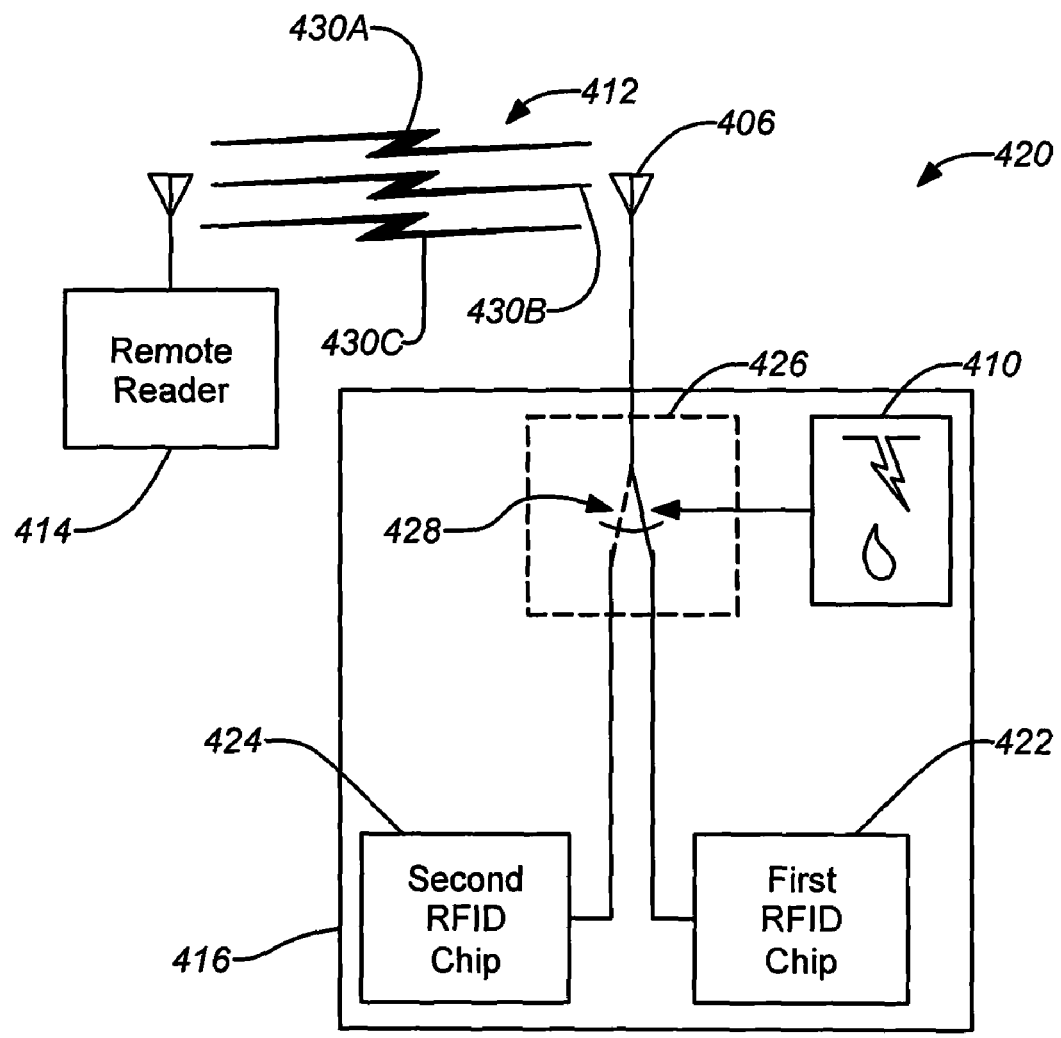
FIG. 4B is a schematic diagram of an exemplary embodiment for structural health sensing employing two RFID chips.

FIG. 4B is a schematic diagram of an exemplary embodiment for structural health sensing employing two RFID chips. Generally, the elements of this system 420 function in the same manner as the system 400 of FIG. 4A except where noted. In this system 420, a first and a second RFID chip 422, 424 are used along with a structural health sensor 426 that includes a switch 428 that toggles the connection to the antenna 406 between the two RFID chips 422, 424 (i.e., functioning as a single pole double throw (SPDT) switch). Thus, the remote reader 414 establishes the wireless communication 412 with the first RFID chip 422 through the antenna 406 connected to the first RFID chip to receive the response signal 430B before the structural problem indicator 410 occurs (in response to the query signal 430A from the remote reader 414). However, after the structural problem indicator 410 has triggered the switch 428, the antenna 406 is toggled to disconnect the first RFID chip 422 and connect the second RFID chip 424 to the antenna. Thus, the remote reader 414 establishes the wireless communication 412 with the second RFID chip 424 through the antenna 406 connected to the second RFID 424 after the structural problem indicator 410 to receive a different response signal 430C. Just as before, the first RFID chip 422 and the second RFID chip 424 (along with the structural health sensor 426) may be passive and powered through the wireless communication from the remote reader 414 using known RFID technology.

As described, the switch 428 of the system 420 is integrated into the sensor 426, which is coupled with the antenna 406. The sensor 426 may be designed to react in the presence of moisture and function as a single-event switch once moisture is detected. Once the moisture comes in contact with the sensor 426, the switch 428 toggles the first RFID chip 422 out of the antenna 406 path while toggling the second RFID chip into the antenna 406 path. Unlike the single RFID chip system 400 described previously, the two RFID chip system 420 provides an extra level of assurance that the tag is working properly. This is because the remote reader 414 receives an affirmative signal 430C from the second RFID chip 424, rather than simply inferring the sensor result from the absence of a response signal 418B as with the first system 400.

6. Exemplary RFID Structural Health Sensor Systems

Figure 5A:
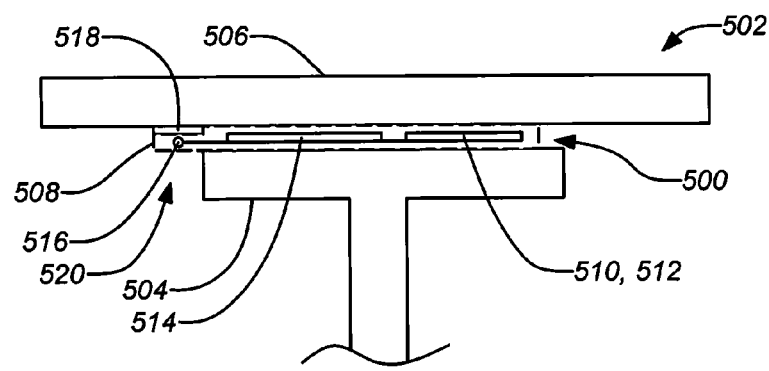
FIGS. 5A & 5B illustrate an exemplary structural health sensor disposed between a metal beam and panel in a structure.
Figure 5B:
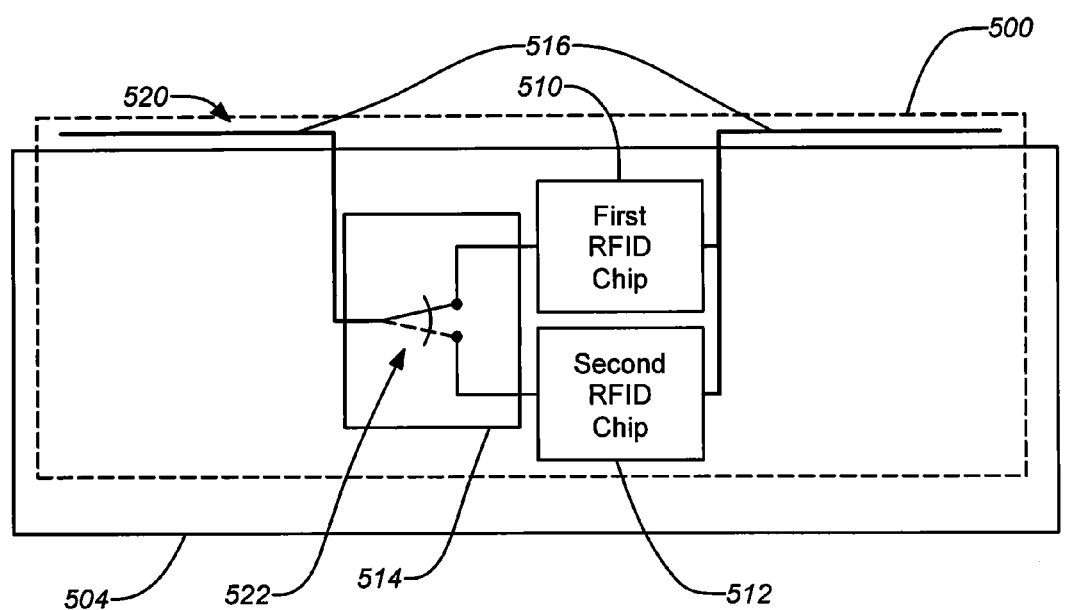

FIGS. 5A & 5B illustrate an exemplary structural health sensor device 500 disposed between a metal beam 504 and panel 506 in a structure 502. FIG. 5A illustrates a side view cross section of the structure 502 showing the sensor device 500. The sensor device 500 comprises one or more nonconductive membrane layers 508 including one or more RFID chips 510, 512, a structural health sensor 514 and antenna 516 and may be disposed in the bolted joint between the beam 504 and panel 506. In some embodiments, the entire sensor device 500 may be incorporated into an RFID tag for ready installation during manufacture of the structure 502.

FIG. 5B illustrates a top view cross section through the sensor 500. In this example, the antenna 516 comprises a two-wire antenna. However, it should be noted that only one of the leads of the two-wire antenna needs to be routed through the structural health sensor for operation of the sensor device 500. The other wire is couple to both the RFID chips 510, 512 as shown. Due to the surrounding metal structural elements, in order to facilitate establishing wireless communication with the remote reader (not shown), the antenna 516 is disposed within a region 520 of the sensor device 500 that is outside of the mechanical joint of the structure 502. In addition, a dielectric material layer 518 may be disposed between the antenna 516 and the metal panel 506 above as shown in FIG. 5A. The sensor device 500 operates in essentially the same manner as the system 420 described in FIG. 4B using structural health sensor 514 that toggle switch 522 between the two RFID chips 510, 512 in response to a structural problem indicator (e.g., moisture). Alternately, one RFID chip can be eliminated to implement the system 400 of FIG. 4A in a similar manner, as will be understood by those skilled in the art.

As described above, sensing devices in accordance with the present disclosure comprise an antenna, one or more RFID chips, sensing components including a switch, and packaging. These elements may be combined on an inlay similar to existing RFID tags. The wireless interface is based on RFID technology, which is a reliable and affordable commodity. There are numerous vendors and designs of RFID chips, antennas, and tag inlays. For the above example, an augmented version of a typical RFID tag may be implemented to yield a system that can detect the presence of moisture or corrosion. The tags may be produced in variable shapes and lengths providing flexibility of installation.

Any of the described devices and systems for structural health sensing can be further enhanced by varying the quantity, location, type and function of sensors on the RFID tag. For instance, adding another sensor on the opposite side of the RFID tag in the system 500 of FIG. 5B would increase the probability of detection since a larger area would be sampled. Ideally, a sensor may span the entire area of the tag area so that the switch can toggle if moisture is encountered at any location on the tag. In some embodiments, different sensor types may also coexist on the same tag. For instance, a single tag may have combined moisture and corrosion detection capability by combining sensors/switches and RFID chips in different configurations. See e.g., U.S. patent application Ser. No. 11/941,367, by Fay et al., filed Nov. 16, 2007, and U.S. patent application Ser. No. 12/202,883, by Fay et al., filed Sep. 2, 2008.

Further, embodiments of the disclosure are not limited to moisture or corrosion detection, but could also include the detection of other structural problem conditions, such as fractures. For example, a sensor could be designed to physically break in the presence of a crack acting as a simple switch. The form factor of the tag can vary significantly to allow for sensing in areas other than faying surfaces. For example, the tag may be integrated with washers or other fastening elements if detection around fastener holes was desired. This design would work in conjunction with others providing a comprehensive sensing capability. See e.g., U.S. patent application Ser. No. 11/941,307, by Fay et al., filed Nov. 16, 2007.

7. Method of Moisture Sensing

Figure 6:
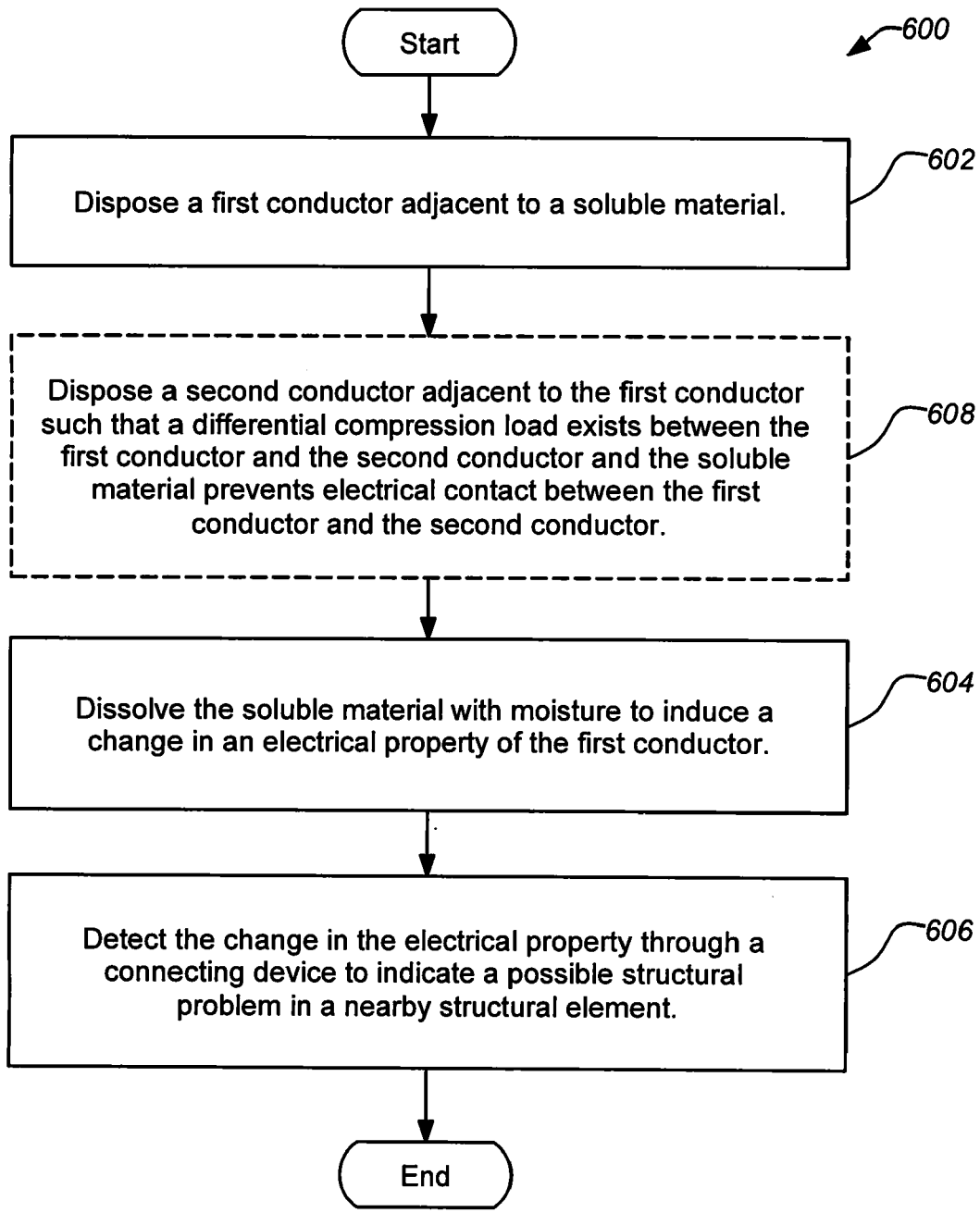
FIG. 6 is a flowchart of a method of sensing moisture to indicate possible corrosion in a nearby structural element.

FIG. 6 is a flowchart of a method 600 of sensing moisture to indicate a possible structural problem (i.e. corrosion) in a nearby structural element. The method 600 begins with an operation 602 of disposing a first conductor adjacent to a soluble material. In operation 604, the soluble material is dissolved with moisture to induce a change in an electrical property of the first conductor. Finally, in operation 606, the change in the electrical property is detected through a connecting device to indicate a possible structural problem in a nearby structural element. Typically, the possible structural problem is corrosion of the nearby metal structural element. This method 600 for sensing moisture may be modified consistent with any of the devices and/or systems described herein. One or more RFID chips in an antenna may be employed in a circuit including the first conductor to create a remotely detectable change in the electrical property as previously described.

In one notable embodiment, optional operation 608 (indicated by the dashed outline) is performed to dispose a second conductor adjacent to the first conductor such that a differential compression load exists between the first conductor and the second conductor and the soluble material prevents electrical contact between the first conductor and the second conductor. In this case, the moisture dissolves the soluble material to allow contact between the first conductor and the second conductor.

This concludes the description of various embodiments of the present invention. The foregoing description including the described embodiment of the disclosure has been presented for the purposes of illustration and description. It is not intended to be exhaustive or to limit embodiments of the invention to the precise forms disclosed. Many modifications and variations are possible within the scope of the foregoing teachings. Additional variations of the present disclosure may be devised without departing from the inventive concept as set forth in the following claims.

What is claimed is:

1. An apparatus, comprising:
a first conductor; and
a soluble material disposed adjacent to the first conductor;
wherein moisture dissolves the soluble material to induce a change in an electrical property of the first conductor detectable through a connecting device indicating a possible structural problem in a nearby structural element;
wherein the first conductor comprises a conductive ink supported by the soluble material and the moisture dissolves the soluble material and thereby disrupts the conductive ink and thereby breaks continuity of the first conductor to induce the change in the electrical property and the first conductor forms an antenna for one or more RFID chips coupled thereto and disruption of the conductive ink induces a change in a wireless response signal from the one or more RFID chips as the change in the electrical property.

2. The apparatus of claim 1, wherein the soluble material comprises polyvinyl alcohol (PVA).

3. The apparatus of claim 1, wherein the soluble material is substantially non-conductive.

4. The apparatus of claim 1, wherein the first conductor and the one or more RFID chips are passive and powered through a wireless remote reader as the connecting device.

5. The apparatus of claim 1, further comprising a second conductor disposed adjacent to the first conductor;
wherein a differential compression load exists between the first conductor and the second conductor and the soluble material prevents electrical contact between the first conductor and the second conductor and the moisture dissolves the soluble material to allow contact between the first conductor and the second conductor to induce the change in the electrical property of the first conductor detectable through the connecting device indicating the possible structural problem in the nearby structural element.

6. The apparatus of claim 5, wherein the first conductor, the second conductor and the soluble material are disposed within a gasket having weep holes that allow the moisture to reach the soluble material.

7. The apparatus of claim 5, wherein the first conductor and the second conductor form an antenna for one or more RFID chips coupled thereto and contact between the first conductor and the second conductor induces a change in a wireless response signal from the one or more RFID chips as the change in the electrical property.

8. The apparatus of claim 7, wherein the first conductor and the second conductor and the one or more RFID chips are passive and powered through a wireless remote reader as the connecting device.

9. A method for sensing moisture, comprising the steps of:
disposing a first conductor adjacent to a soluble material;
dissolving the soluble material with moisture to induce a change in an electrical property of the first conductor; and
detecting the change in the electrical property through a connecting device to indicate a possible structural problem in a nearby structural element;
wherein the first conductor comprises a conductive ink supported by the soluble material and the moisture dissolves the soluble material and thereby disrupts the conductive ink and thereby breaks continuity of the first conductor to induce the change in the electrical property and the first conductor forms an antenna for one or more RFID chips coupled thereto and disruption of the conductive ink induces a change in a wireless response signal from the one or more RFID chips as the change in the electrical property.

10. The method of claim 9, wherein the soluble material comprises polyvinyl alcohol (PVA).

11. The method of claim 9, wherein the soluble material is substantially non-conductive.

12. The method of claim 9, wherein the first conductor and the one or more RFID chips are passive and powered through a wireless remote reader as the connecting device.

13. The method of claim 9, further comprising disposing a second conductor adjacent to the first conductor such that a differential compression load exists between the first conductor and the second conductor and the soluble material prevents electrical contact between the first conductor and the second conductor;
wherein the moisture dissolves the soluble material to allow contact between the first conductor and the second conductor to induce the change in the electrical property of the first conductor detectable through the connecting device indicating the possible structural problem in the nearby structural element.

14. The method of claim 13, wherein the first conductor, the second conductor and the soluble material are disposed within a gasket having weep holes that allow the moisture to reach the soluble material.

15. The method of claim 13, wherein the first conductor and the second conductor form an antenna for one or more RFID chips coupled thereto and contact between the first conductor and the second conductor induces a change in a wireless response signal from the one or more RFID chips as the electrical property change.

16. The method of claim 15, wherein the first conductor and the second conductor and the one or more RFID chips are passive and powered through a wireless remote reader as the connecting device.

* * * * *